(12) United States Patent
Wagner et al.

(10) Patent No.: US 6,247,933 B1
(45) Date of Patent: Jun. 19, 2001

(54) DENTAL IMPLANT DELIVERY SYSTEM

(75) Inventors: William R. Wagner, Escondido; Jeffrey A. Bassett, Vista, both of CA (US)

(73) Assignee: Sulzer Dental Inc., Carlsbad, CA (US)

( * ) Notice: Subject to any disclaimer, the term of this patent is extended or adjusted under 35 U.S.C. 154(b) by 0 days.

(21) Appl. No.: 09/458,811

(22) Filed: Dec. 10, 1999

(51) Int. Cl.[7] ................................................ A61C 8/00
(52) U.S. Cl. ................................................ 433/173
(58) Field of Search .................. 433/172, 173, 433/174, 175, 176

(56) References Cited

U.S. PATENT DOCUMENTS

| | | | |
|---|---|---|---|
| 3,990,438 | 11/1976 | Pritchard | 128/92 |
| 4,027,392 | 6/1977 | Sawyer et al. | 32/10 |
| 4,177,562 | 12/1979 | Miller et al. | 133/174 |
| 4,234,309 | 11/1980 | Sellers | 433/225 |
| 4,259,072 | 3/1981 | Hirabayashi et al. | 433/173 |
| 4,553,942 | 11/1985 | Sutter | 433/225 |
| 4,655,711 | 4/1987 | Weissman | 433/225 |
| 4,712,681 | 12/1987 | Branemark et al. | 206/438 |
| 4,713,003 | 12/1987 | Symington et al. | 433/173 |
| 4,758,161 | 7/1988 | Niznick | 433/173 |
| 4,763,788 | 8/1988 | Jorneus et al. | 206/438 |
| 4,802,848 | 2/1989 | Randin | 433/225 |
| 4,856,648 | 8/1989 | Krueger | 206/63.5 |
| 4,856,994 | 8/1989 | Lazzara et al. | 433/173 |
| 4,915,629 | 4/1990 | Sellers | 433/173 |
| 4,927,363 | 5/1990 | Schneider | 433/173 |
| 4,955,811 | 9/1990 | Lazzara et al. | 433/173 |
| 4,976,617 | 12/1990 | Carchidi | 433/141 |
| 4,988,297 | 1/1991 | Lazzara et al. | 433/173 |
| 4,995,810 | 2/1991 | Soderberg | 433/141 |
| 5,018,970 | 5/1991 | Stordahl | 433/75 |
| 5,026,285 | 6/1991 | Durr et al. | 433/173 |
| 5,030,095 | 7/1991 | Niznick | 433/173 |
| 5,030,096 | 7/1991 | Hurson et al. | 433/173 |
| 5,035,619 | 7/1991 | Daftary | 433/173 |
| 5,062,800 | 11/1991 | Niznick | 433/229 |
| 5,073,111 | 12/1991 | Daftary | 433/173 |
| 5,076,788 | 12/1991 | Niznick | 433/173 |
| 5,100,323 | 3/1992 | Friedman et al. | 433/173 |
| 5,106,300 | 4/1992 | Voitik | 433/173 |
| 5,108,288 | 4/1992 | Perry | 433/173 |
| 5,125,840 | 6/1992 | Durr et al. | 433/173 |
| 5,145,372 | 9/1992 | Daftary et al. | 433/173 |
| 5,167,664 | 12/1992 | Hodorek | 606/73 |
| 5,180,303 | 1/1993 | Hornburg et al. | 433/173 |
| 5,197,881 | 3/1993 | Chalifoux | 433/173 |
| 5,209,659 | 5/1993 | Friedman et al. | 433/173 |

(List continued on next page.)

FOREIGN PATENT DOCUMENTS

001727808 A1   4/1992  (SU) .

OTHER PUBLICATIONS

Spline Dental Implant System Technical Products Addendum, Cat. No. 4717, 6/96, pp. SP–15 and SP–16.

Primary Examiner—Nicholas D. Lucchesi
(74) Attorney, Agent, or Firm—Philip S. Lyren

(57) ABSTRACT

A dental implant system that dramatically simplifies implantation of a dental implant at an implant site. The dental implant system includes a threaded dental implant having a mounting end with an internal, threaded, axial bore. A healing cap is threadably engaged with the internal, axial bore prior to implantation. The healing cap also includes engagement features, such as a plurality of indentations, that permit secure engagement of a dental driving tool with the healing cap. Thus, upon engagement with a dental driving tool, the dental implant system can be threaded into engagement with the alveolar bone at the implant site and covered by gingival tissue, without any additional components or process steps.

35 Claims, 11 Drawing Sheets

U.S. PATENT DOCUMENTS

| | | | |
|---|---|---|---|
| 5,281,140 | 1/1994 | Niznick | 433/172 |
| 5,282,746 | 2/1994 | Sellers et al. | 433/172 |
| 5,297,963 | 3/1994 | Dafatry | 433/172 |
| 5,312,254 | 5/1994 | Rosenlicht | 433/173 |
| 5,316,476 | 5/1994 | Krauser | 433/173 |
| 5,322,443 | 6/1994 | Beaty | 433/141 |
| 5,336,090 | 8/1994 | Wilson, Jr. et al. | 433/172 |
| 5,338,196 | 8/1994 | Beaty et al. | 433/172 |
| 5,362,235 | 11/1994 | Daftary | 433/172 |
| 5,366,374 | 11/1994 | Vlassis | 433/165 |
| 5,368,160 | 11/1994 | Leuschen et al. | 206/339 |
| 5,413,480 * | 5/1995 | Musikant et al. | 433/173 |
| 5,415,545 | 5/1995 | Shaw | 433/173 |
| 5,431,567 | 7/1995 | Daftary | 433/172 |
| 5,437,550 | 8/1995 | Beaty et al. | 433/141 |
| 5,437,551 | 8/1995 | Chalifoux | 433/173 |
| 5,449,291 | 9/1995 | Lueschen et al. | 433/173 |
| 5,468,150 | 11/1995 | Brammann | 433/173 |
| 5,482,463 | 1/1996 | Wilson, Jr. et al. | 433/173 |
| 5,484,285 | 1/1996 | Morgan et al. | 433/173 |
| 5,538,428 | 7/1996 | Staubli | 433/173 |
| 5,580,246 | 12/1996 | Fried et al. | 433/172 |
| 5,582,299 | 12/1996 | Lazzara et al. | 206/63.5 |
| 5,622,500 | 4/1997 | Niznick | 433/173 |
| 5,630,717 | 5/1997 | Zuest et al. | 433/172 |
| 5,704,788 | 1/1998 | Milne | 433/173 |
| 5,733,123 | 3/1998 | Blacklock et al. | 433/173 |
| 5,755,575 | 5/1998 | Biggs | 433/173 |
| 5,897,319 | 4/1999 | Wagner et al. | 433/174 |
| 5,927,979 * | 7/1999 | Misch et al. | 433/173 |
| 6,068,480 * | 5/2000 | Misch et al. | 433/173 |
| 6,083,004 * | 7/2000 | Misch et al. | 433/173 |
| 6,086,371 * | 7/2000 | Bassett et al. | 433/173 |

* cited by examiner

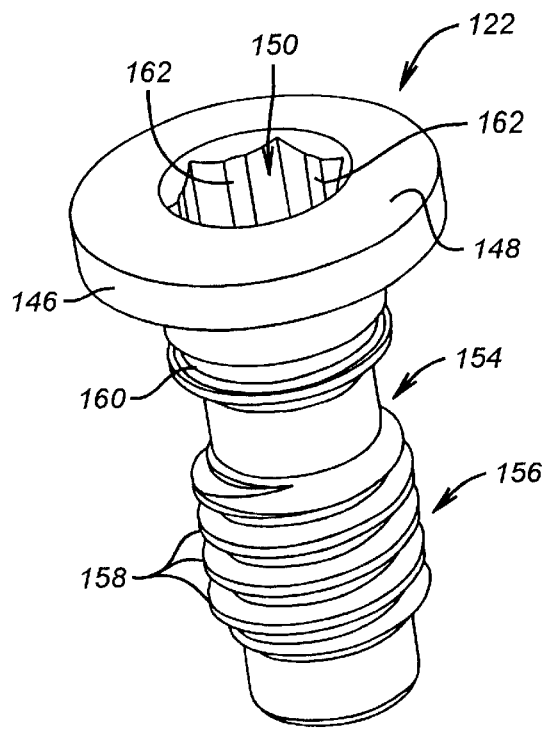
FIG. 11
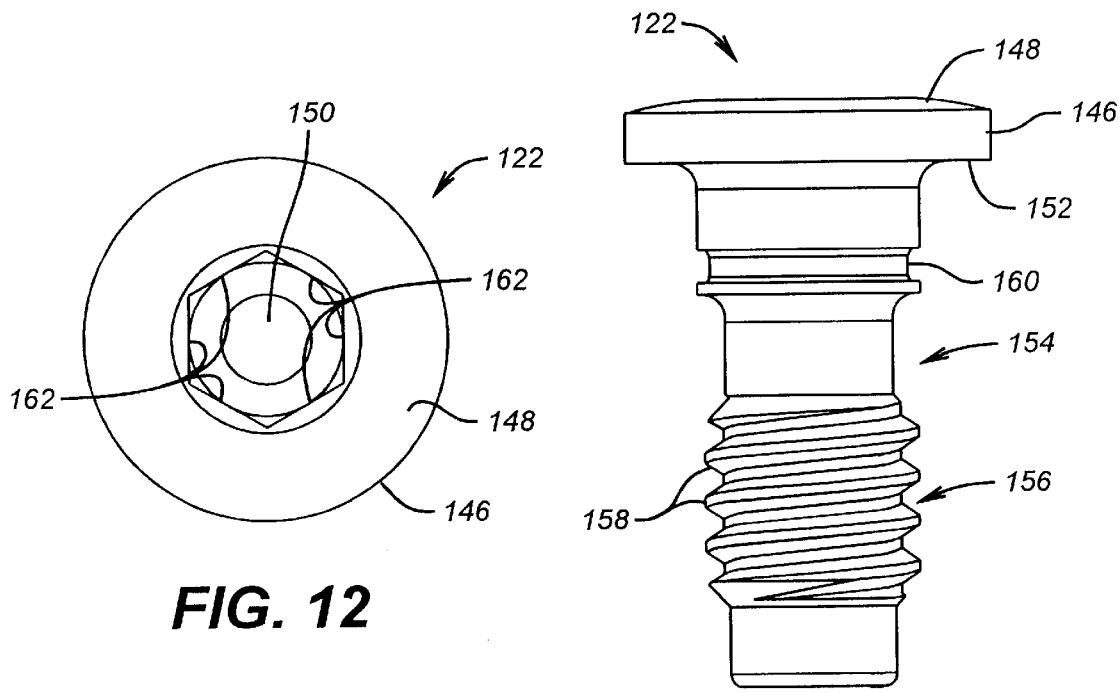
FIG. 12
FIG. 13

DENTAL IMPLANT DELIVERY SYSTEM

FIELD OF THE INVENTION

The present invention relates generally to dental implants, and particularly to a dental implant system and method in which a healing cap and implant driving features are combined to eliminate procedural steps and simplify implantation.

BACKGROUND OF THE INVENTION

Dental implants typically are packaged and shipped as a component of an implant delivery system. The delivery system generally includes a vial containing an implant, such as a threaded implant, a driver mount, a healing screw and a vial cap. Sometimes, the dental implant is removably connected to the vial cap to facilitate removal from the vial prior to implantation.

The dental implant, driver mount and healing screw must be maintained in a sterile environment prior to implantation. Accordingly, the dental implant components are shipped in sterile packaging that may be opened during a surgical implantation procedure.

To install or implant the dental implant, an implant site is prepared using conventional surgical methodology. For example, an incision is made along the gingival tissue at the implant site. Then, a cylindrical bore is drilled into the alveolar bone, and the bore is tapped to receive a conventional threaded implant or left untapped for receipt of a self-tapping implant.

After the implant site is prepared, the vial cap and vial are separated to permit removal of the dental implant, driver mount and healing screw. At this point, a driving tool, such as a motorized dental hand-piece, is connected to the free end of the driver mount via an adapter. The dental implant and driver mount are moved to the implant site, and the end of the implant is driven into the cylindrical bore formed in the alveolar bone.

Following placement of the dental implant in the bore, the driver mount must be removed from the implant, and the healing screw is then threaded into the coronal end of the implant. It should be noted that in some delivery systems, the healing screw is used to maintain the driver mount in engagement with the dental implant. In this latter system, the healing screw must be removed to permit removal of the driver mount and then rethreaded into the coronal end of the implant.

Following placement of the healing screw, the gingival tissue is sutured to cover the dental implant. The implant remains implanted in the jawbone for several months to permit osseointegration and healing to occur. During a second surgical procedure, the implant is reexposed and the healing screw is removed. An abutment is affixed to the top of the implant, and a dental prosthesis is attached to the abutment.

During placement of the dental implant, it is extremely advantageous to reduce the number of steps required and the number of components handled. Therefore, it would be desirable to eliminate use of the driver mount and to eliminate the removal, placement and threading of the healing screw into the coronal end of the implant prior to suturing of the gingival tissue to cover the dental implant.

Attempts have been made to integrate a healing cap or cover with the dental implant prior to implantation to simplify the implantation procedure. However, it has proved difficult to securely attach the healing cap in a manner that permits a dental driving tool to engage either the dental implant itself or the healing cap for driving the implant into the implant site. Providing a preattached healing cap is particularly difficult when the dental implant includes mounting protrusions, such as splines, at its coronal end.

Furthermore, a typical dental implant includes an axial, threaded bore at its mounting end to facilitate secure mounting of the abutment and prosthesis. Conventional healing screws are threaded into this bore during the period of osseointegration. A threaded engagement with a complete healing cap having dental tool driving features, however, also requires rotational motion which can be problematic. The splines or protrusions can hinder the rotational motion required to seat the healing cap.

It would be advantageous to have a healing cap that could be preattached to a dental implant in a secure fashion to permit it to be directly engaged by a dental driving tool. Such a system would dramatically simplify the implantation of the dental implant by effectively allowing the implantation to be performed in a single step. Upon engagement of such a healing cap with a dental driving tool, the practitioner would simply thread the dental implant into place at the implant site. No other steps would be required, with respect to the dental implant, because the healing cap already would be in place and ready for covering by the gingival tissue during the period of osseointegration.

The present invention addresses the drawbacks of the prior art, and provides the desired solution described in the paragraph above.

SUMMARY OF THE INVENTION

The present invention relates generally to a dental implant delivery system. The system comprises a dental implant having an exterior threaded region, designed to engage bone, and a mounting end having a threaded axial opening. The system further includes a complete healing cap engaged with the threaded axial opening. The healing cap has an outer perimeter and a driving tool engagement feature including a plurality of indentations positioned to engage a driving tool. Exemplary indentations are slots that extend radially inward from the outer perimeter.

According to another aspect of the invention, a dental implant delivery system is provided. The system includes a vial having an interior and an opening through which the interior is accessible. A vial cover is disposed over the opening. A dental implant is disposed in the interior and includes a threaded region and a mounting end. The mounting end includes a threaded axial opening. A complete healing cap is mounted to the mounting end and threadably engaged with the threaded axial opening. Additionally, the complete healing cap has a driving tool engagement feature that utilizes a plurality of slots.

According to another aspect of the invention, a method is provided for simplifying the implantation of a dental implant of the type having an outer threaded region, a mounting end, and an axial, threaded opening in the mounting end. The method includes forming a healing cap having a plurality of dental tool engagement features, such as indentations. The method further includes covering the axial, threaded opening with the healing cap prior to implantation of the dental implant at an implantation site. Further, the method includes securing the healing cap to the dental implant by, for example, threaded engagement with the axial, threaded opening.

According to another aspect of the invention, a method is provided for implanting a dental implant system in a predrilled hole within a recipient's jawbone. The method includes engaging a driving tool with the healing cap of a preassembled dental implant system. The combined healing cap and dental implant are moved to the predrilled hole via the driving tool to eliminate the need for separate handling of components. The healing cap is then utilized in rotating the dental implant into the predrilled hole. Following implantation, the driving tool is disengaged from the healing cap.

BRIEF DESCRIPTION OF THE DRAWINGS

The invention will hereafter be described with reference to the accompanying drawings, wherein like reference numerals denote like elements, and:

FIG. 11 is a perspective view of the healing screw illustrated in FIG. 4;

FIG. 12 is a top view of the healing screw illustrated in FIG. 11;

FIG. 13 is a front view of the healing screw illustrated in FIG. 11;

DESCRIPTION OF THE PREFERRED EMBODIMENTS

Figure 1:
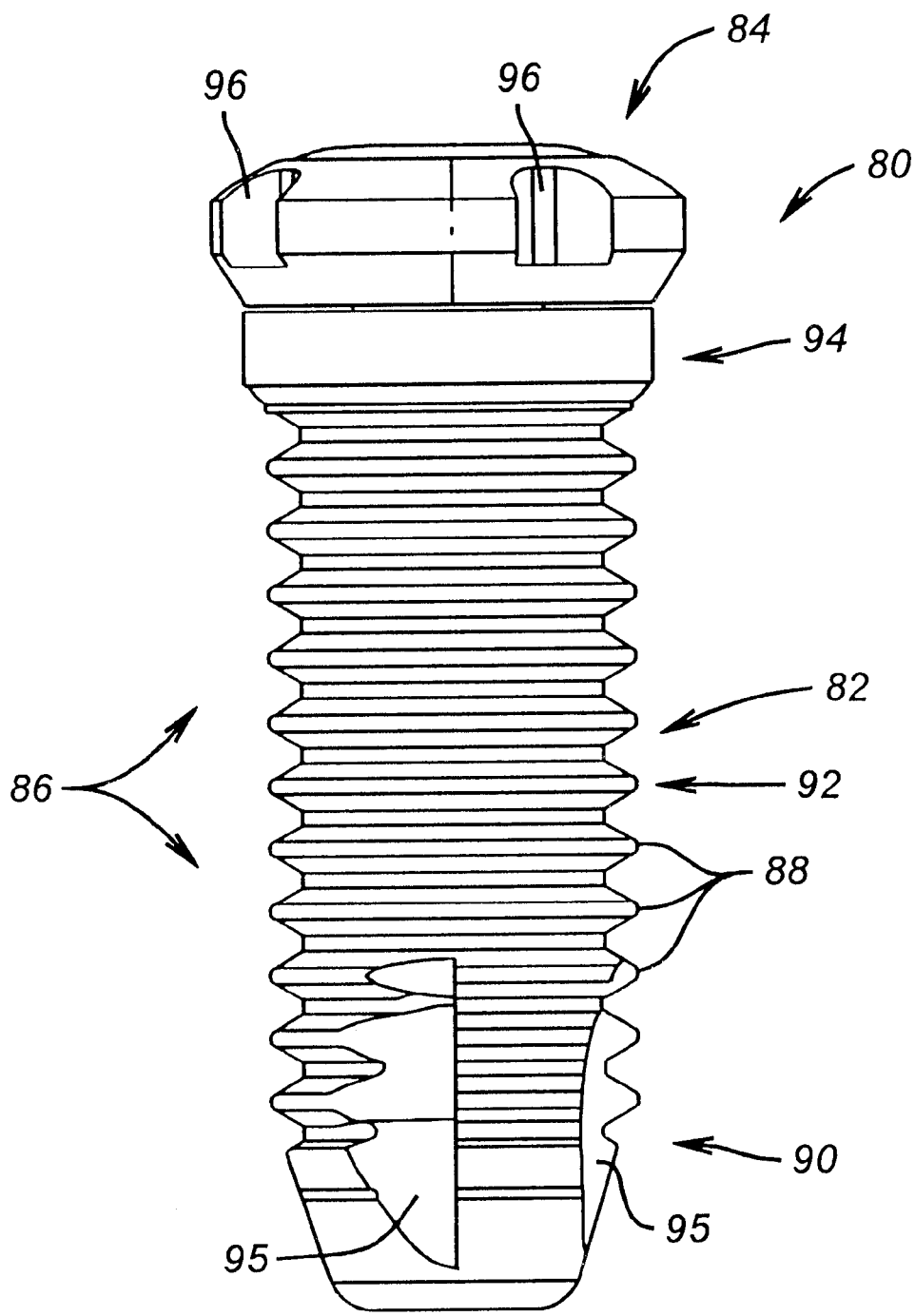
FIG. 1 is a front view of a dental implant system, according to a preferred embodiment of the present invention.

Referring generally to FIG. 1, a dental implant system 80 is illustrated, according to a preferred embodiment of the present invention. Dental implant system 80 is prepared as a completed module that may be implanted into the alveolar bone of an individual. The implantation is accomplished without the removal, addition or altering of components prior to the implant system being covered by gingival tissue and allowed to undergo a period of osseointegration, e.g. a three month period, in preparation for mounting of the prosthetic tooth.

Dental implant system 80 is an integral, preassembled unit including a dental implant 82 and a healing cap 84. Dental implant 82 typically includes a threaded region 86 having threads 88. In the embodiment illustrated, threaded region 86 extends from a distal end 90 through a middle region 92 to a coronal or mounting end 94. However, other thread patterns and configurations can be utilized with dental implant 82. Additionally, dental implant 82 can be a self-tapping implant having appropriate self-tapping features, such as flutes 95. One such self-tapping implant having appropriate self-tapping features is disclosed in U.S. Pat. No. 5,897,319.

Healing cap 84 is securely attached to mounting end 94 of dental implant 82. Healing cap 84 includes an implant driving tool engagement feature 96 designed to matingly receive an engagement end 98 of a dental implant driving tool 100 (see FIG. 2). Implant driving tool 100 may be connected to a powered driver, as is commonly used in standard implantation procedures.

Figure 2:
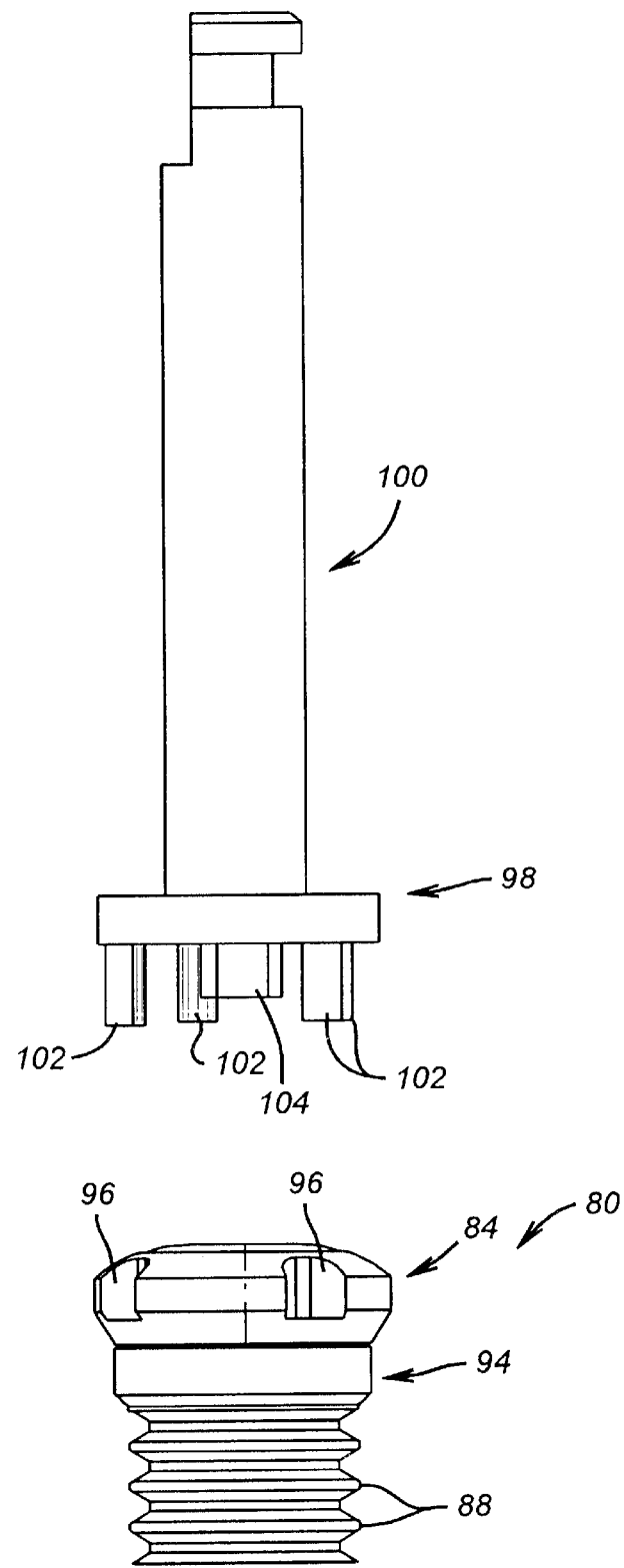
FIG. 2 is a front view of the dental implant system of FIG. 1 with a driving tool.

In the exemplary embodiment shown in FIG. 2, engagement end 98 of implant driving tool 100 includes a plurality of male protrusions 102 that are sized and arranged for engagement with healing cap 84 and the holding of dental implant system 80. Furthermore, engagement end 98 may include a central engagement member 104 also disposed for engagement with healing cap 84. The design of engagement end 98 helps assure that dental implant system 80 remains connected to implant driving tool 100 as the dental implant 82 is moved to an implant site, e.g. a predrilled bore in the alveolar bone of a patient receiving the dental implant.

Figure 3:
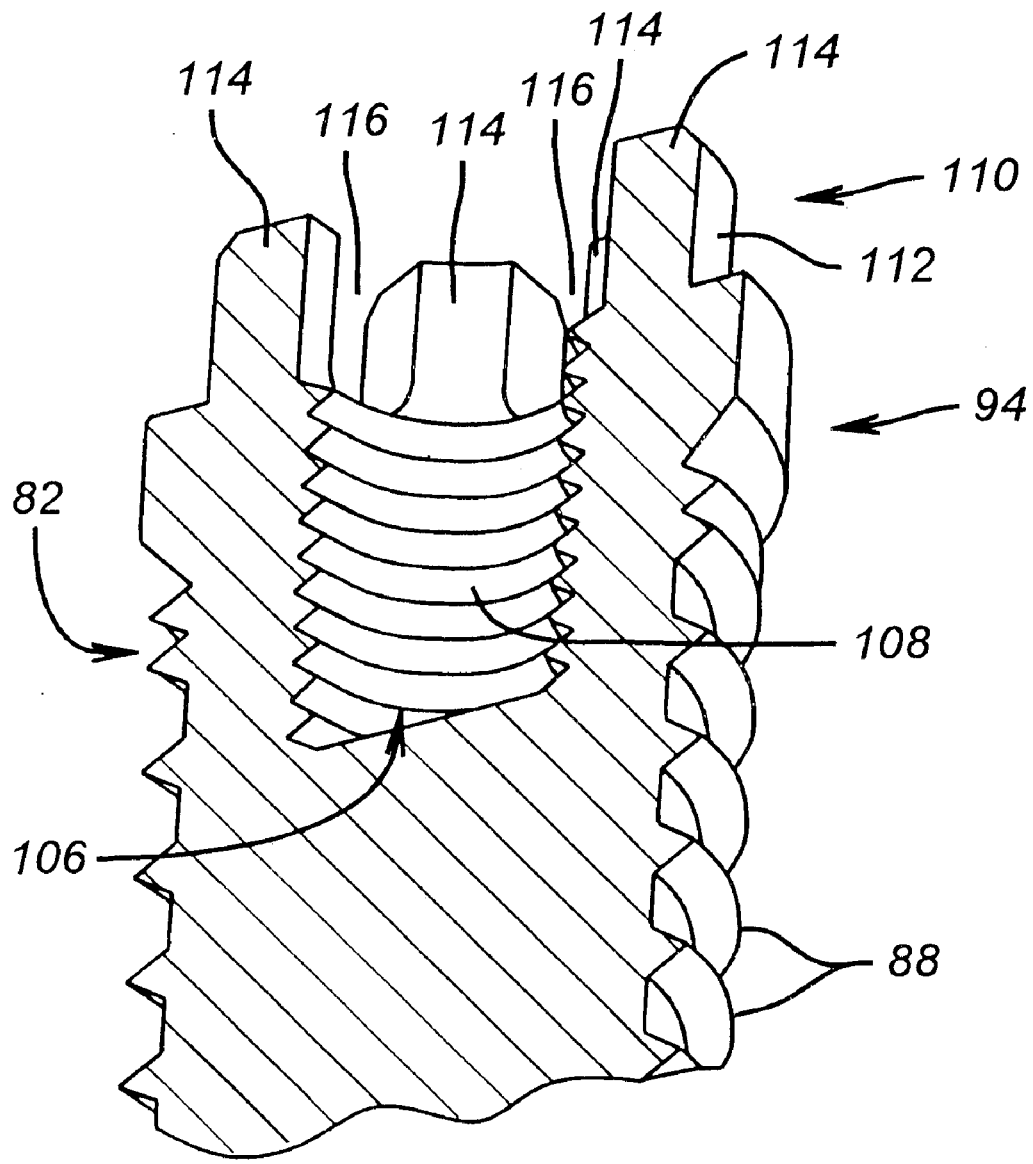
FIG. 3 is an axial cross-section of a mounting of an exemplary dental implant utilized in a preferred embodiment of the present invention.
Figure 4:
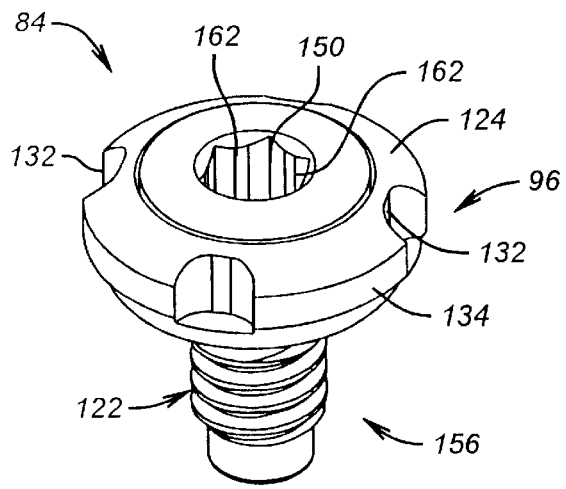
FIG. 4 is a perspective view of the healing cap illustrated in FIG. 1.
Figure 5:
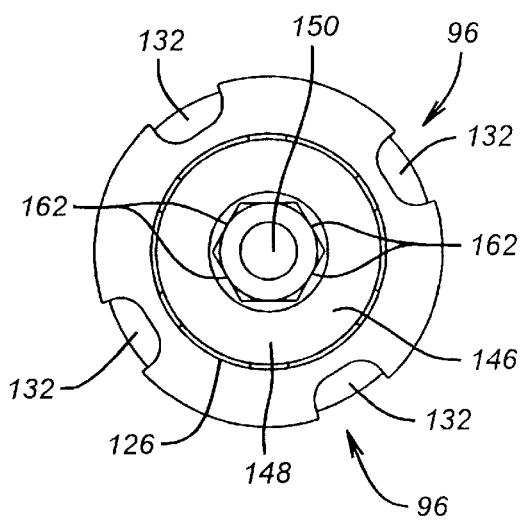
FIG. 5 is a top view of the healing cap illustrated in FIG. 4.
Figure 6:
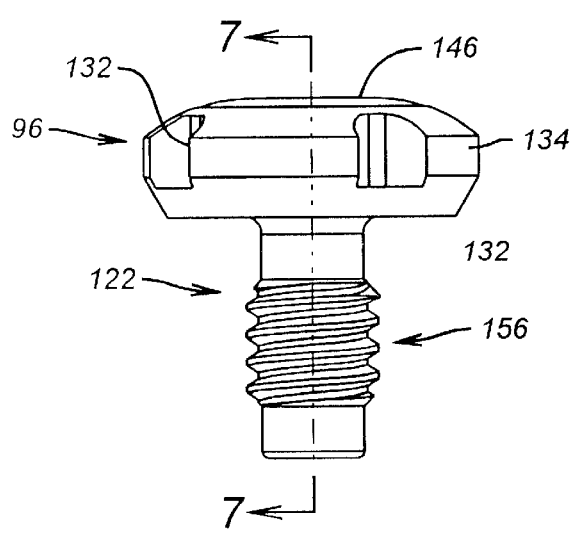
FIG. 6 is a front view of the healing cap illustrated in FIG. 4.
Figure 7:
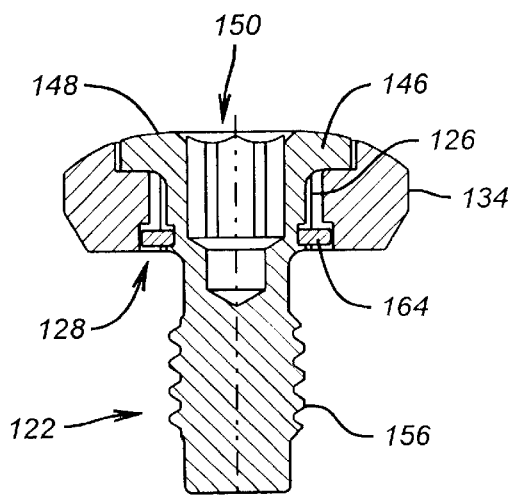
FIG. 7 is a cross-sectional view taken generally along line 7—7 of FIG. 6.

As illustrated in FIG. 3, mounting end 94 of dental implant 82 preferably includes an internal, axial opening 106. Axial opening 106 includes a threaded region 108 that extends along at least a portion of axial opening 106. Additionally, mounting end 94 includes a protrusion 110 disposed about axial opening 106 and extending in a direction generally opposite the axial direction of opening 106. Protrusion 110 may completely encircle axial opening 106 and have an outer surface 112 that is polygonal, e.g. hexagonal in shape. Furthermore, protrusion 110 may comprise multiple protrusions in the form of alternating splines 114 and gaps 116. The protrusion 110, e.g., splines 114, cooperate with healing cap 84 to apply the torque necessary to turn or thread dental implant 82 into the alveolar bone at the implant site, as will be explained more fully below. Alternatively, protrusion 110 may be a negative protrusion in the form of a recess or recesses disposed in mounting end 94 about axial opening 106.

Referring now to FIGS. 4–7, healing cap 84 is illustrated according to one preferred embodiment of the present invention. In this embodiment, healing cap 84 includes a healing screw 122 and a healing cuff 124. Healing screw 122 is rotatably mounted in an axial opening 126 formed through healing cuff 124. A retainer 128 prevents inadvertent separation of healing screw 122 from healing cuff 124.

Figure 8:
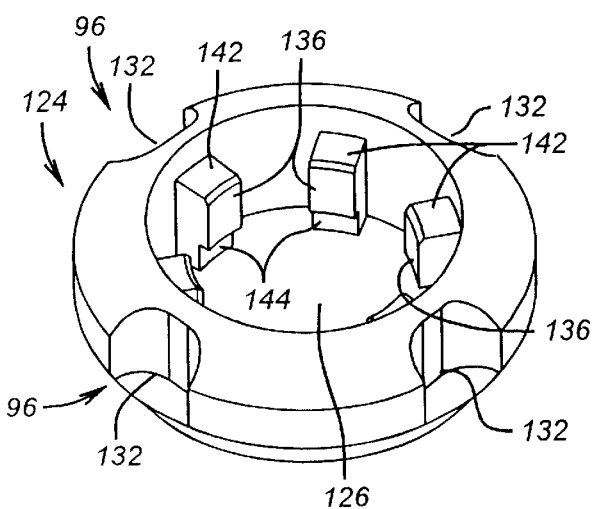
FIG. 8 is a perspective view of the healing cuff illustrated in FIG. 4.
Figure 9:
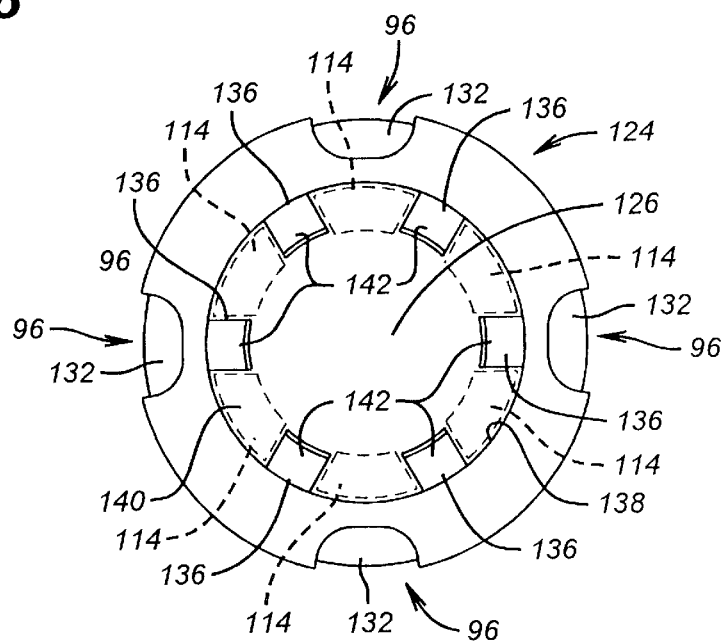
FIG. 9 is a top view of the healing cuff illustrated in FIG. 8.
Figure 10:
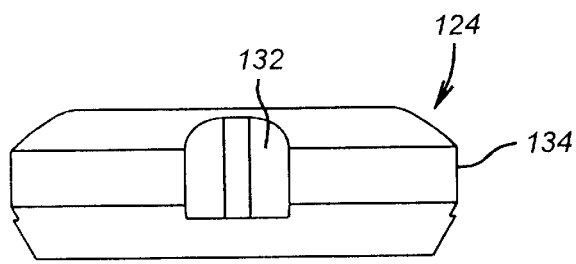
FIG. 10 is a front view of the healing cuff illustrated in FIG. 8.

With additional reference to FIGS. 8, 9 and 10, a preferred, exemplary embodiment of healing cuff 124 can be described. Healing cuff 124 includes a dental tool engagement feature 96 that is designed to engage a conventional dental implant driving tool, such as driving tool 100, that has an appropriate, corresponding engagement end to engage tool engagement feature 96. In the illustrated embodiment, dental tool engagement feature 96 includes a plurality of indentations 132 that extend inwardly from an outer perimeter 134. As shown in FIG. 9, a plurality of indentations 132, e.g. four indentations, are generally arcuate and disposed at equally spaced intervals along outer perimeter 134. In this embodiment, dental tool engagement feature 96 is symmetrical. In other words, indentations 132 may be engaged by an appropriate dental driving tool for rotation of healing cuff 124 in either a clockwise or a counterclockwise direction.

Additionally, healing cuff 124 includes a plurality of dividers or torque inducement members 136 that extend radially inward into axial opening 126 from a generally circular inner wall 138. Torque inducement members 136 define a plurality of spaces or recesses 140 disposed therebetween. Recesses 140 are disposed to receive protrusion 110, and specifically splines 114, of dental implant 82. As described above, members 136 fit within gaps 116 to apply torque against splines 114 when dental tool engagement feature 96 is engaged and turned by a dental driving tool (see FIG. 9). In the event protrusion 110 is formed as a negative protrusion, i.e. a recess, then space or spaces 140 are replaced by a positive protrusion or protrusions that are sized for receipt by the negative protrusion 110.

In the particular embodiment illustrated, the plurality of torque inducement members 136 each includes a top surface 142 that, in combination, serve as a shelf for receiving healing screw 122. Preferably, each torque inducement member 136 also includes a notch 144 disposed on an end generally opposite top surface 142. Notch portion 144 facilitates retention of healing screw 122 in axial opening 126, as further described below.

Referring also to FIGS. 11, 12 and 13, a preferred embodiment of healing screw 122 is illustrated. Healing screw 122 includes an upper flanged portion 146. Upper flanged portion 146 comprises a top surface 148 through which a central opening 150 extends, and a bottom surface 152. Bottom surface 152 rests on the top support surfaces 142 of the plurality of torque inducement members 136 when healing screw 122 and healing cuff 124 are assembled into the completed healing cap 120.

Healing screw 122 also includes a stem 154 that extends generally axially from upper flanged portion 146. Stem 154 includes a threaded region 156 having appropriate threads 158 to engage the threaded axial opening 106 of a corresponding dental implant 82. Additionally, stem 154 includes a circumferential groove 160 disposed between threaded region 156 and upper flanged portion 146.

Central opening 150 preferably extends in an axial direction through upper flanged portion 146 and into an interior of stem 154. The central opening is designed to receive a tool that can be used to rotate healing screw 122 when healing cap 120 is mounted to or removed from its corresponding dental implant 82. A plurality of internal sides 162 are arranged to create, for instance, a generally hexagonal opening to receive a hexagonal tool.

In the embodiment illustrated, retainer 128 includes the cooperating configurations of healing screw 122 and healing cuff 124 in combination with a ring clip 164. Specifically, healing screw 122 is inserted through axial opening 126 of healing cuff 124. The bottom surface 152 of upper flanged portion 146 rests against the top surface 142 of torque inducement members 136. Additionally, ring clip 164 is mounted in circumferential groove 160 and extends radially outwardly into notch 144 formed in each of the torque inducement members 136 generally opposite their top surfaces 142. Thus, healing screw 122 is free to rotate with respect to healing cuff 124, but the interference between flanged portion 146 and top surface 142 as well as the interference between ring clip 164 and notch portion 144 prevent separation of healing screw 122 and healing cuff 124.

Figure 14:
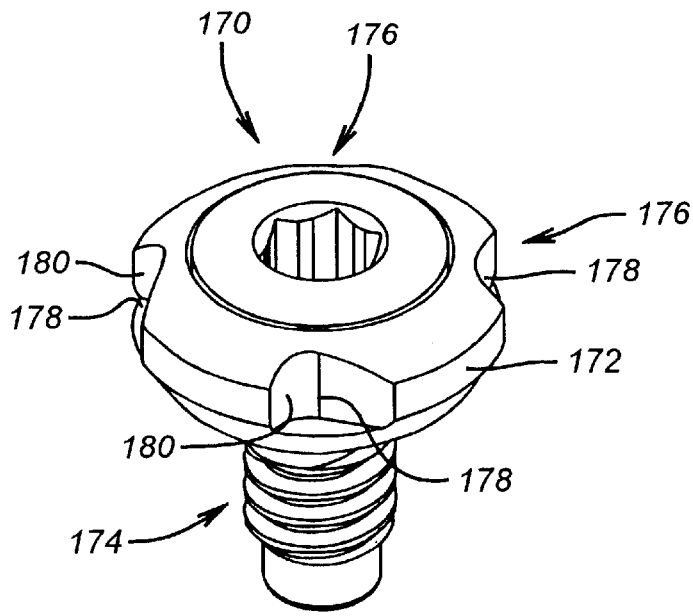
FIG. 14 is a perspective of another alternate embodiment of the healing cap illustrated in FIG. 1.
Figure 15:
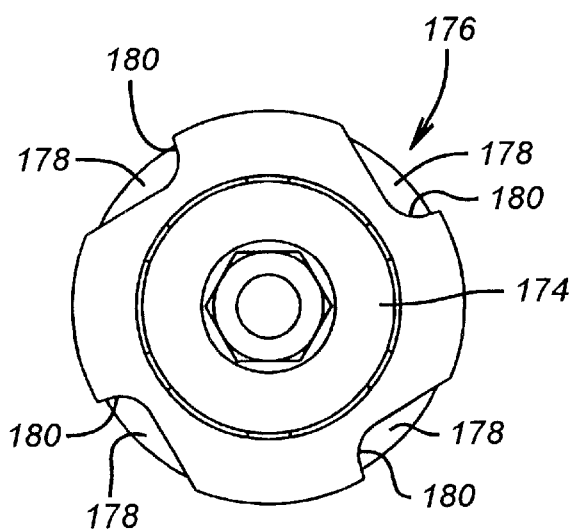
FIG. 15 is a top view of the healing cap illustrated in FIG. 14.

Referring generally to FIGS. 14 and 15, an alternate embodiment of healing cap 84 is illustrated. In this embodiment, a healing cap 170 includes a healing cuff 172 and a healing screw 174. Healing cuff 172 and healing screw 174 are similar in design to the healing cuff 124 and healing screw 122 described with reference to FIGS. 4–13. Accordingly, healing cuff 172 and healing screw 174 will not be described in detail except for the features that are dissimilar.

In the embodiment illustrated, healing cap 170 includes an asymmetric dental tool engagement feature 176. Asymmetric engagement feature 176 comprises a plurality of indentations 178 that extend radially inward towards healing screw 174 from an outer perimeter of healing cap 170. For example, there may be four indentations 178 that each have an engagement wall 180. Engagement wall 180 permits rotation of healing cuff 172 in a single direction only, e.g. clockwise. Thus, a dental driving tool may be engaged with healing cuff 172 to implant the dental implant 82, but it cannot be used to turn the dental implant in the opposite direction.

Figure 16:
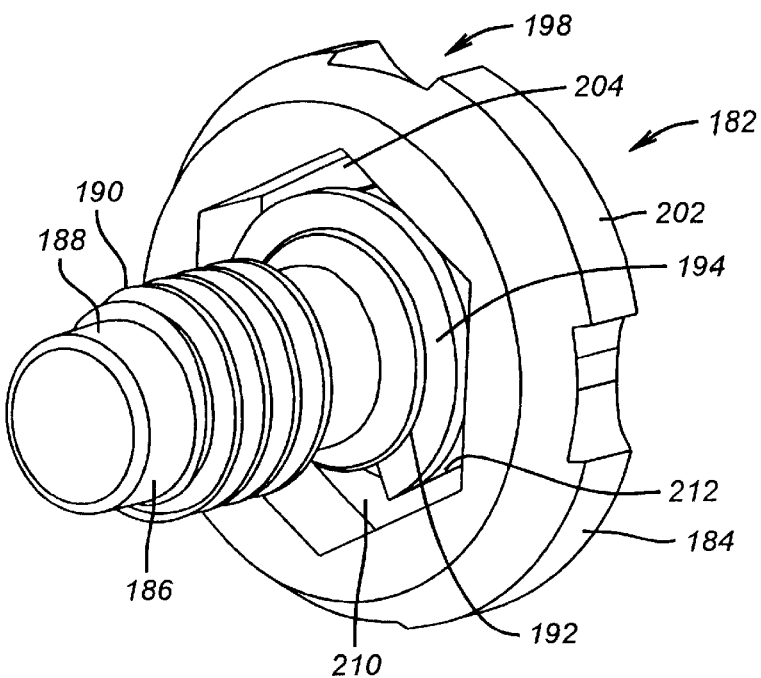
FIG. 16 is a bottom, perspective view of an alternate embodiment of the healing cap illustrated in FIG. 1.
Figure 17:
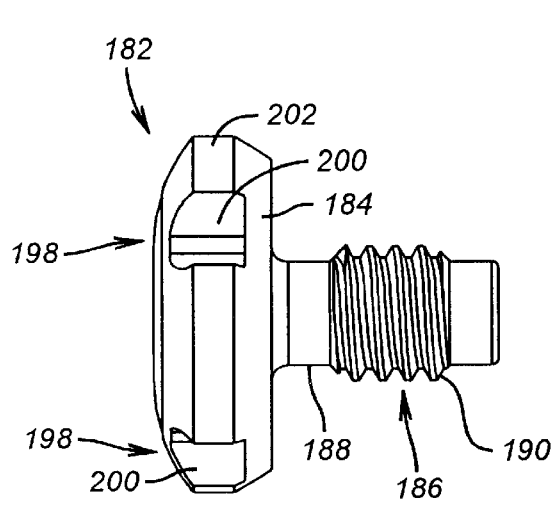
FIG. 17 is a front view of the healing cap illustrated in FIG. 16.
Figure 18:
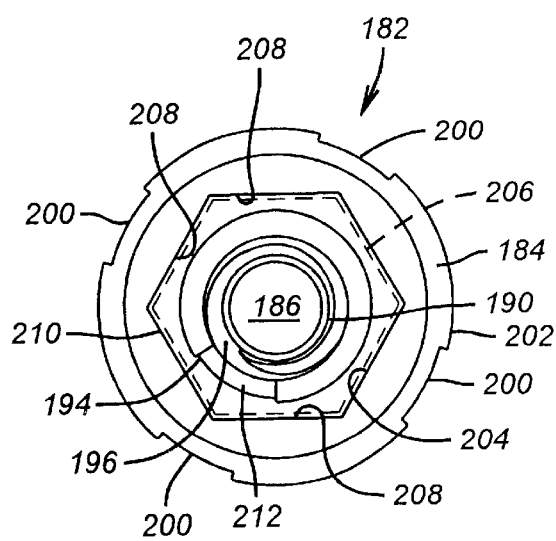
FIG. 18 is a bottom view of the healing cap illustrated in FIG. 16.
Figure 19:
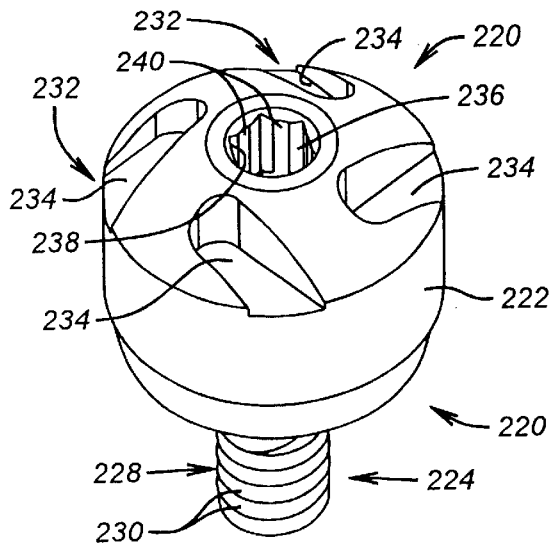
FIG. 19 is a perspective view of another alternate embodiment of the healing cap illustrated in FIG. 1.
Figure 20:
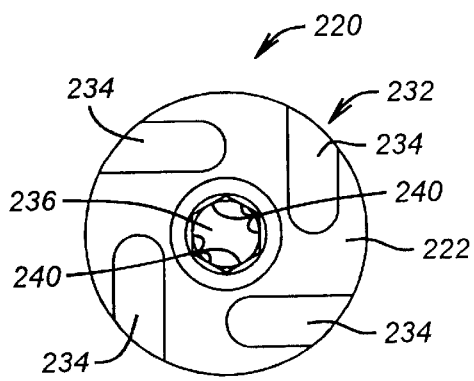
FIG. 20 is a top view of the healing cap illustrated in FIG. 19.
Figure 21:
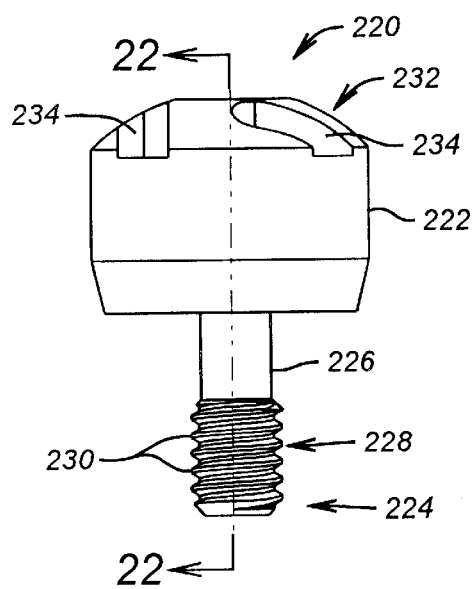
FIG. 21 is a front view of the healing cap illustrated in FIG. 19.

Referring generally to FIGS. 16, 17 and 18, another alternate embodiment of healing cap 84 is illustrated. In this embodiment, a healing cap 182 includes a healing cuff 184 and a healing screw 186.

Healing screw 186 is similar to the healing screw described in FIGS. 11–13 and generally includes a stem 188 having a threaded region 190. Stem 188 also includes a groove 192 for receiving a clip ring 194. Stem 188 extends axially from an upper flanged portion 196, as described above with reference to FIG. 13.

Healing cuff 184 includes a dental tool engagement feature 198 that may include a plurality of indentations 200 extending radially inward from an outer perimeter 202. Opposite indentations 200, healing cuff 184 includes a recess 204 configured to receive protrusion 110 of dental implant 82. In this embodiment, however, recess 204 is polygonal in shape for receiving a polygonal protrusion, such as the hexagonal protrusion 206 represented by dashed lines in FIG. 18. Recess 204 is defined by a plurality of sides 208, e.g. six sides 208, that impart torque to dental implant 82 via an appropriate protrusion, such as hexagonal protrusion 206. Alternatively, the recess can be replaced by a polygonal protrusion designed for receipt in a corresponding recess formed in the mounting end of the dental implant.

Recess 204 is defined further by an upper wall 210 that is disposed generally transverse to walls 208. Upper wall 210 includes an opening 212 through which healing screw 186 is rotatably mounted. However, upper wall 210 also serves as a barrier between clip ring 194 and flanged portion 196 of healing screw 186 to ensure that the healing screw is not inadvertently separated from the healing cuff.

Referring now to FIGS. 19, 20, 21 and 22, another alternate embodiment of healing cap 84 is illustrated. In this embodiment, a healing cap 220 includes an integrally formed healing cuff 222 and healing screw 224. Healing screw 224 comprises a shaft 226 affixed to and extending axially from healing cuff 222. Shaft 226 includes a threaded region 228 having a plurality of threads 230 designed for threaded engagement with threaded region 108 in axial opening 106 of dental implant 82.

Healing cuff 222 includes a dental tool engagement feature 232. Engagement feature 232 comprises a plurality of elongate indentations 234. In the illustrated embodiment, the indentations 234 extend generally in the direction of required rotation for implantation. This renders the indentations asymmetric in the sense that they will impart torque to the dental implant in a single direction only. Additionally, a central opening 236 is disposed between indentations 234. Central opening 236 includes a wrench engaging portion 238 that may be formed, for instance, as a hexagonal opening defined by six sides 240. Wrench engagement portion 238 may be used in conjunction with an appropriate tool to remove healing cap 220 from the dental implant 82 after the period of osseointegration.

Figure 22:
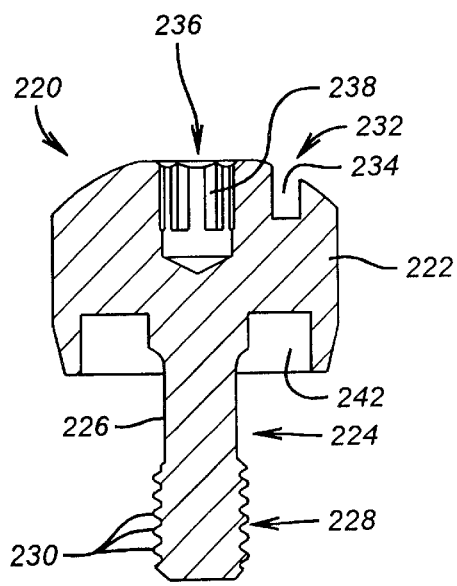
FIG. 22 is a cross-sectional view taken generally along line 22—22 of FIG. 21.

In this embodiment, healing cap 220 also includes a recessed area 242 extending about shaft 226, as illustrated best in FIG. 22. Recessed area 242 is designed to receive a protrusion 110, such as splines 114. In this embodiment, healing cap 220 is threaded into axial opening 106 of dental implant 82 until healing cuff 222 is firmly positioned against mounting end 94. The combined dental implant 82 and healing cap 220 then can readily be implanted at the desired implant site. Again, there is no need to remove, add or change any components prior to covering dental implant 82 and healing cap 220 with gingival tissue during the period of osseointegration.

Figure 23:
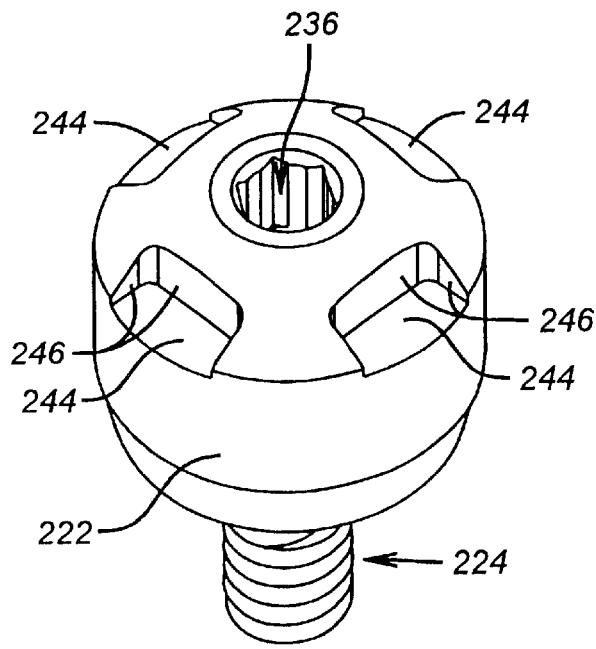
FIG. 23 is a perspective view of another alternate embodiment of the healing cap illustrated in FIG. 1.
Figure 24:
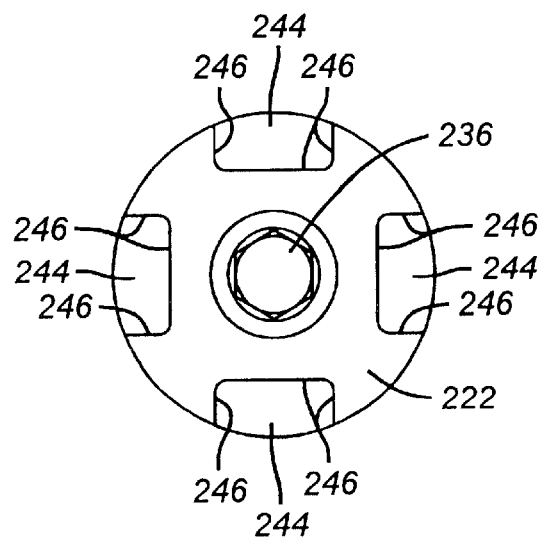
FIG. 24 is a top view of the healing cap illustrated in FIG. 23.

Another embodiment of healing cap 220 is illustrated in FIGS. 23 and 24. This embodiment includes the same features as healing cap 220 illustrated in FIGS. 19–22, except for differently styled indentations 234. As illustrated, the healing cap includes symmetric indentations 244 that are generally rectangular. Each symmetrical indentation 244 includes three sides or walls 246 arranged to receive an appropriate dental driving tool. It should be noted that the specific configurations of indentations used in FIGS. 19 and 23 also can be used with the earlier described embodiments and vice versa.

Figure 25:
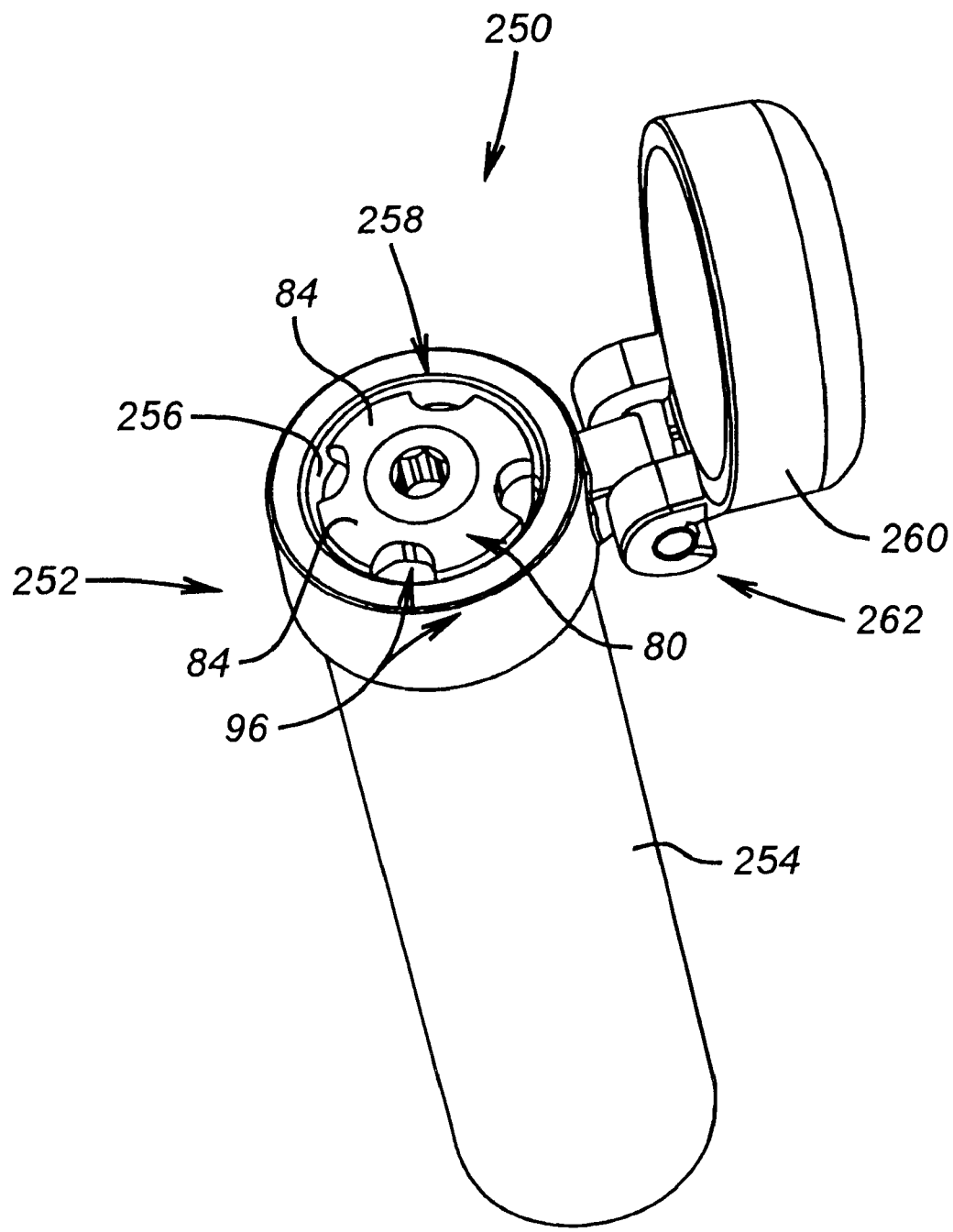
FIG. 25 is a perspective view of a vial for holding a dental implant according to preferred embodiment of the present invention.

Referring to FIG. 25, an exemplary embodiment of an overall dental implant delivery system 250 is illustrated. A wide variety of delivery systems potentially can be used to package the dental implant systems described above. Preferably, the overall dental implant delivery system 250 utilizes a vial or other container that can be opened to expose the healing cap and driving tool engagement feature. This permits the practitioner to simply engage the driving tool engagement feature of the healing cap with a dental driving tool. The entire preassembled dental implant system then can be moved to the implant site and implanted with no further manipulations of implant related components.

One embodiment of a vial 252 is illustrated in FIG. 25. For the purpose of explanation, delivery system 250 is described as vial 252 in combination with dental implant system 80, having dental implant 82 and healing cap 84. However, other dental implants and healing caps can be disposed within and utilized with vial 252.

Vial 252 includes an elongated cylindrical body 254 having a hollow interior cavity 256. Elongate cylindrical body 254 includes an opening 258 that is covered by a vial cover 260. Vial cover 260 preferably is connected to elongate cylindrical body 254 by a hinge 262 disposed proximate opening 258 and external to hollow interior 256.

Dental implant system 80 is disposed within hollow interior 256. The dental implant 82 is inserted into hollow interior 256 first such that healing cap 84, and specifically the driving tool engagement feature, e.g. feature 96, is directly accessible through opening 258. Vial cover 260 is pivoted to a closed position over opening 258 to enclose dental implant system 80. Preferably, the hollow interior 256 is sealed and dental implant system 80 is maintained in a sterile environment until implantation.

During the implantation procedure, a practitioner opens vial cover 260 to expose healing cap 84 and driving tool engagement feature 96. Vial cover 260 remains connected to elongate cylindrical body 254 via hinge 262 to prevent a dropped or lost vial cover. After opening vial cover 260, an implant driving tool, such as dental implant driving tool 100, is engaged with driving tool engagement feature 96 of healing cap 84. The preattached healing cap 84 and dental implant 82 then are removed and implanted at an implant site in a single step. There is no need for a driver mount, or a separate healing screw that must be removed and reinserted into axial opening 106 of dental implant 82. The preattached healing cap 84 is complete, and the gingival tissue can be sutured to cover dental implant system 80 during the required period of osseointegration.

It will be understood that the foregoing description is of preferred embodiments of this invention, and that the invention is not limited to the specific forms shown. For example, a variety of healing cap designs and driving tool engagement feature configurations can be utilized; a variety of biocompatible materials can be used as known to those of ordinary skill in the art; the mounting end of the dental implant may have splines, polygonal protrusions, and various other engagement features; the dental implant may include self-tapping features; and the vial may be constructed in a variety of configurations. These and other modifications may be made in the design and arrangement of the elements without departing from the scope of the invention as expressed in the appended claims.

What is claimed is:

1. A dental implant delivery system, comprising:
    a dental implant having an exterior threaded region designed to engage bone, and a mounting end having a threaded axial opening; and
    a complete two-piece healing cap engaged with the threaded axial opening, the healing cap including a healing cuff with an axial bore and a healing screw with a threaded external shaft passing through the axial bore, the healing cuff rotatably mounted around the healing screw, and the healing cuff having an outer perimeter and a driving tool engagement feature including a plurality of indentations positioned to engage a driving tool.

2. The dental implant delivery system as recited in claim 1, wherein the plurality of indentations extend generally radially inward from the outer perimeter.

3. The dental implant delivery system as recited in claim 1, wherein the plurality of indentations comprise asymmetric slots.

4. The dental implant delivery system as recited in claim 1, wherein the plurality of indentations comprise symmetric slots.

5. The dental implant delivery system as recited in claim 4, wherein the symmetric slots extend generally radially inward from the outer perimeter.

6. The dental implant delivery system as recited in claim 1, wherein the healing cuff includes a plurality of dividers adapted to transmit torque to the dental implant wherein the dividers extend in the axial bore.

7. The dental implant delivery system as recited in claim 6, wherein the complete healing cap includes a retainer to prevent separation of the healing cuff and the healing screw.

8. The dental implant delivery system as recited in claim 6, wherein the mounting end includes a protrusion and the healing cap includes a recess to receive the protrusion such that the complete healing cap and the dental implant rotate together when a torque is applied to the driving tool engagement feature.

9. The dental implant delivery system as recited in claim 8, wherein the protrusion and the recess are hexagonal and sized for engagement.

10. The dental implant delivery system as recited in claim 6, wherein the mounting end includes a recess and the complete healing cap includes a protrusion oriented to engage the recess when the dental implant and the complete healing cap are engaged, such that the dental implant and the complete healing cap rotate together when a torque is applied to the driving tool engagement feature.

11. The dental implant delivery system as recited in claim 10, wherein the protrusion and the recess are hexagonal and sized for engagement.

12. The dental implant delivery system as recited in claim 1, wherein the complete healing cap also includes an axially located tool engagement feature.

13. The dental implant delivery system as recited in claim 12, wherein the tool engagement feature is recessed and generally hexagonal in cross-section.

14. The dental implant delivery system as recited in claim 1, wherein the mounting end includes a protrusion and the healing cap includes a recess to receive the protrusion such that the complete healing cap and the dental implant rotate together when a torque is applied to the driving tool engagement feature.

15. The dental implant delivery system as recited in claim 14, wherein the protrusion and the recess are hexagonal and sized for engagement.

16. The dental implant delivery system as recited in claim 14, wherein the protrusion comprises a plurality of splines and the recess comprises a plurality of spline recesses sized to receive the plurality of splines.

17. The dental implant delivery system as recited in claim 1, wherein the mounting end includes a recess and the complete healing cap includes a protrusion oriented to engage the recess when the dental implant and the complete healing cap are engaged, such that the dental implant and the complete healing cap rotate together when a torque is applied to the driving tool engagement feature.

18. A dental implant delivery system, comprising:
a vial having an interior and an opening through which the interior is accessible;
a vial cover disposed to cover the opening;
a dental implant disposed in the interior, the dental implant having a threaded region and a mounting end, the mounting end including a threaded axial opening; and
a complete healing cap having two components; a healing screw with a threaded external shank adapted to engage the threaded axial opening of the dental implant, and a healing cuff rotatably mounted around the healing screw.

19. The dental implant delivery system as recited in claim 18, wherein the healing screw and healing cap are formed of two separate pieces that are removably connectable together, wherein the healing cuff includes an axial bore with an internal ledge and the healing screw includes a peripheral flange adapted to abut the ledge while the healing screw and healing cuff are mounted together.

20. The dental implant delivery system as recited in claim 19, wherein the complete healing cap includes a retainer disposed to prevent separation of the healing cuff and healing screw.

21. A method for simplifying the implantation of a dental implant having an outer threaded region, a mounting end, and an axial, threaded opening in the mounting end, comprising:
providing a healing cap formed from two pieces, wherein a healing cuff has a bore and a healing screw has an external threaded shaft, the healing cuff adapted to freely rotate around a proximal end of the healing screw with the threaded shaft extending through the bore;
covering the axial, threaded opening with the healing cap prior to implantation of the dental implant at an implantation site; and
screwing the threaded shaft of the healing screw into the threaded opening of the implant while the healing cuff is mounted to the healing screw and anti-rotationally engaged with the mounting end of the implant.

22. The method as recited in claim 21 further comprising the step of providing the healing cuff with a plurality of external engaging features.

23. The method as recited in claim 22, further comprising:
engaging a driving tool with the external engaging features;
moving the dental implant and healing cap to the implantation site via the driving tool; and
driving the implant into the implantation site with the driving tool, wherein the driving tool transfers torque directly to the engaging features and then the healing cuff transfers torque to the mounting end of the implant.

24. The method as recited in claim 24, further comprising:
leaving the healing cap engaged with the dental implant during a period of osseointegration prior to attachment of the prosthesis.

25. The method as recited in claim 22, further comprising constructing the healing cap with a healing screw rotatably mounted in a healing cuff; and retaining the healing screw at its position of rotation in the healing cuff.

26. The method as recited in claim 22, further comprising:
providing a protrusion on the mounting end of the dental implant; and
creating a recess in the healing cap to received the protrusion.

27. A method for implanting a dental implant system in a predrilled hole in a recipients jawbone, without assembly or disassembly of implant components, the dental implant system including a healing cap threadably engaged with a dental implant, the method comprising:
providing the healing cap with two separate components: a healing cuff and a healing screw, wherein the healing screw has an elongated cylindrical configuration with a threaded external shank at a distal end and wherein the healing cuff has a cylindrical shape with an axial bore, with the healing cuff being rotatably mounted around a proximal end of the healing screw;

engaging a driving tool with the healing cap;

moving the healing cap and the dental implant to the predrilled hole via the driving tool;

rotating the dental implant into the predrilled hole via the healing cap; and disengaging the driving tool from the healing cap.

28. The method as recited in claim 27, further comprising leaving the healing cap threadably engaged with the dental implant during a period of osseointegration.

29. The method as recited in claim 27, further comprising:

providing the healing cuff with a ledge in the axial bore;

providing the healing screw with a head portion at the proximal end; and abutting the head portion against the ledge while the healing cuff and healing screw are assembled.

30. The method as recited in claim 29, further comprising retaining the healing screw and the healing cuff in engagement with one another by a retainer to prevent inadvertent separation.

31. The method as recited in claim 29, further comprising:

creating a protrusion on a mounting end of the dental implant; and creating a corresponding recess in the healing cuff to receive the protrusion, such that torque may be imparted to the dental implant via the healing cap.

32. The method as recited in claim 27, further comprising forming an asymmetric implant driving tool engagement feature in the healing cap.

33. The method as recited in claim 32, wherein forming includes forming a plurality of slots that extend radially inward from an outer perimeter.

34. The method as recited in claim 27, further comprising forming a symmetric implant driving tool engagement feature in the healing cap.

35. The method as recited in claim 34, wherein forming includes forming a plurality of slots that extend radially inward from an outer perimeter.

\* \* \* \* \*